(12) United States Patent
Lynch

(10) Patent No.: US 8,900,178 B2
(45) Date of Patent: Dec. 2, 2014

(54) METHOD AND APPARATUS FOR A SELF-VENTING ENDOSCOPIC BIOMATERIAL APPLICATOR

(71) Applicant: Patrick Lynch, Camarillo, CA (US)

(72) Inventor: Patrick Lynch, Camarillo, CA (US)

(*) Notice: Subject to any disclaimer, the term of this patent is extended or adjusted under 35 U.S.C. 154(b) by 0 days.

(21) Appl. No.: 13/854,037

(22) Filed: Jul. 3, 2013

(65) Prior Publication Data

US 2014/0012184 A1 Jan. 9, 2014

Related U.S. Application Data

(60) Provisional application No. 61/667,906, filed on Jul. 3, 2012.

(51) Int. Cl.
*A61M 37/00* (2006.01)
*A61M 11/02* (2006.01)
*A61M 13/00* (2006.01)

(52) U.S. Cl.
CPC ............... *A61M 11/02* (2013.01); *A61M 13/00* (2013.01)
USPC .......................................................... 604/26

(58) Field of Classification Search
CPC ............. A61M 2202/0476; A61M 2210/0693; A61M 1/32; A61M 5/14; A61M 13/003; A61M 1/1698; A61M 1/1678; A61B 18/06; A61B 17/3474; A61F 11/00
USPC ................................................. 604/19, 24, 26
See application file for complete search history.

(56) References Cited

U.S. PATENT DOCUMENTS

| | | | |
|---|---|---|---|
| 4,299,221 A | 11/1981 | Phillips et al. | |
| 5,053,012 A * | 10/1991 | Edwards et al. | 604/146 |
| 5,514,087 A * | 5/1996 | Jones | 604/26 |
| 5,607,391 A | 3/1997 | Klinger et al. | |
| 6,165,201 A * | 12/2000 | Sawhney et al. | 606/214 |
| 7,025,755 B2 | 4/2006 | Epstein | |
| 7,682,336 B2 * | 3/2010 | Hoogenakker et al. | 604/146 |
| 7,842,013 B2 | 11/2010 | Haberland et al. | |
| 7,988,657 B2 | 8/2011 | Shapiro et al. | |
| 2010/0168779 A1 | 7/2010 | Redl et al. | |

* cited by examiner

*Primary Examiner* — Manuel Mendez
(74) *Attorney, Agent, or Firm* — Kafantaris Law Offices; Theo Kafantaris

(57) ABSTRACT

The present invention will provide an endoscopic biomaterial applicator used during laparoscopic surgical procedures that utilizes pressurized gas to facilitate the spray application of a biomaterial while safely and automatically venting the additional volume of gas introduced into the abdominal cavity by endoscopic biomaterial applicator. This is accomplished utilizing a manifold, a plurality of channels, an elongated housing, a spray tip, a cannula gasket, and a gas release valve.

12 Claims, 9 Drawing Sheets

METHOD AND APPARATUS FOR A SELF-VENTING ENDOSCOPIC BIOMATERIAL APPLICATOR

CROSS-REFERENCE TO RELATED APPLICATIONS

This application claims the benefit of U.S. Provisional Patent Application No. 61/667,906, filed on Jul. 3, 2012, and incorporated herein by reference.

STATEMENT REGARDING FEDERALLY SPONSORED RESEARCH AND DEVELOPMENT

Not Applicable.

FIELD OF THE INVENTION

This invention relates to an endoscopic biomaterial applicator, and more particularly, to an applicator that can self-vent gas introduced by the endoscopic applicator while providing a spray application of a biomaterial.

DISCUSSION OF RELATED ART

Generally, surgical procedures produce a great deal of trauma for the human body, as large incisions are used to permit access to the internal tissue that requires attention. Modern advancements in surgical procedures have given rise to minimally invasive surgeries, where small incisions are used and the stress on the human body is reduced. One popular type of minimally invasive surgery is laparoscopic surgery, where operations on the abdomen are performed through small incisions and surgical devices are inserted into the body, permitting the surgeon to operate using digital images displayed on a monitor.

The advantages of laparoscopic surgery include reduced post-operative pain, bleeding, and reduction in external tissue scarring due to the smaller incisions. Laparoscopic surgery is typically conducted by inserting surgical trocar devices from the outside of the body into the abdominal space. Once these trocar devices are in place, they provide the access from the outside of the body to the intra-abdominal space to introduce cameras and surgical equipment. Furthermore, the trocars also provide a port to connect an insufflator.

During laparoscopic surgeries, biomaterials are commonly used to improve control of surgical bleeding, sealing tissue to prevent gas or liquid leakage, adhering tissue planes together, or alternatively preventing tissue planes from adhering to each other. Biomaterials exist in many different forms, from biologic materials to synthetic components, and the compositions vary from one part systems to multi-part systems. Biomaterial must be introduced into the body using biomaterial applicators, which vary in configuration for each surgery and biomaterial type. Applicators vary from simple drip applicators to gas-assisted spray devices.

With multi-component biomaterials that require thorough mixing at the time of application, gas-assisted propulsion of these biomaterials in a spray deposition has been used with favorable results. With some biomaterials, the faster and more homogenous the components are mixed, the quicker the adherence or polymerization time. Further, the spray application of the biomaterial can cover more tissue area than a conventional drip application of the biomaterial, resulting in more economic and practical utilization of the biomaterial.

An insufflator is a gas ventilator based system used in laparoscopic surgery, where a gas is used to inflate the intra-abdominal cavity with an inert gas, most commonly CO2 gas, in order to distend the abdominal cavity. This provides the surgeon with the necessary space and access to the underlying tissues and organs which need attention. The insufflator connects to one of the available trocars having a gas port, where the insufflator introduces the gas to the abdominal cavity. The insufflator will introduce a flow rate of gas and attempt to maintain this intra-abdominal pressure throughout the procedure.

As gas leaks from the abdominal cavity, the insufflator will increase the flow rate of gas, and as the pressure rises above the selected pressure setpoint, the insufflator will remove gas from the abdominal cavity. The pressure necessary to achieve the appropriate surgical space for the surgeon can vary by procedure, but the common intra-abdominal pressure used for laparoscopic surgery is 15 mm Hg. Any pressures higher than this common pressure level can increase the risk of gas embolization to the patient. This is due to the gas passing through the patient's tissue membranes and into the blood stream as the pressure gradient increases. $CO_2$ gas is commonly used for this technique because the human blood stream can absorb this gas type much better than other mediums, such as atmospheric air or nitrogen. However, even $CO_2$ gas can be toxic to a human if high levels are absorbed into the blood stream.

Conventional trocar devices only permit one surgical instrument to be introduced through its working channel at one time. However, new trocar device technology with several working channels are emerging where the trocar can accept multiple surgical devices at one time. This permits fewer surgical incisions into the patient's abdomen while still providing the surgeon the appropriate surgical environment to conduct the procedure. This surgical approach is commonly referred to as single incision laparoscopic surgery (SILS).

With gas-assisted spray applicators that also introduce gas into the abdominal cavity in order to provide spray delivery of the biomaterial, this can pose problems for maintaining a safe intra-abdominal pressure. If the flow rate of gas introduced by the biomaterial applicator is greater than the capacity of the insufflator to remove this sudden volume introduction of gas, the intra-abdominal pressure can rise above the desired intra-abdominal pressure setpoint, and subject the patient to potential gas embolism. Therefore, it is ideal for a biomaterial applicator that uses pressurized gas to enable spray delivery of the biomaterial to possess the ability to help remove any excess volume of gas that it introduces.

U.S. Pat. No. 7,682,336 to Hoogenakker et al, hereinafter Hoogenakker, discloses an apparatus for mixing and administering two non-homogenous liquids to tissue in an endoscopic procedure where the apparatus includes a biomaterial spray applicator, a gas regulator system that attaches to the spray applicator with a tubing line, and a tubing vent line that attaches to the gas valve of a surgical trocar and back to the regulator. When the regulator is actuated by a foot pedal to provide a flow of gas from the regulator to the spray applicator, the spray applicator then deposits the biomaterial inside the body cavity in a spray format enhanced by the gas from the regulator. At the same time that the foot pedal is depressed to actuate gas flow rate, the regulator opens up a valve allowing gas to exit the surgical trocar through the tubing vent line.

The first limitation of Hoogenakker is that it requires an independent gas regulator to provide the gas venting function required to reduce the risk of over-pressurization of the abdominal cavity. The gas regulator resides on the non-sterile side the surgical operating room, and as such, the tubing that connects the sterile biomaterial applicator and trocar back to the regulator must be passed to the non-sterile side of the operating room for connection to the regulator. This can pose cumbersome logistical issues in an operating room environment and also requires the coordination between two operating room personnel to make the tubing connections. Furthermore, when objects are passed back and forth between the sterile side and non-sterile side of an operating room, additional risks related to infection can occur.

The second limitation of Hoogenakker is that the venting function of this system requires the available use of a gas vent port on a surgical trocar. In any laparoscopic procedure, one surgical trocar must be dedicated to the connection to the insufflator in order to distend the abdominal cavity. However, if other trocars are used in the procedure, these trocars commonly do not include a gas vent port to reduce the cost of the trocar. Furthermore, for single incision laparoscopic procedures (SILS), only one trocar is used in the procedure and the single available gas port on the trocar must be used by the insufflator, providing no means to connect a biomaterial spray applicator venting feature that requires this trocar gas port to effectively perform its venting function.

U.S. Patent application. No. US20100168779A1 to Redl et al, hereinafter Redl, discloses a laparoscopic tissue sealant spray apparatus and system having a laparoscopic tissue sealant spray assembly combined with a trocar assembly, where the tissue sealant spray assembly has an elongate delivery tube. The trocar assembly includes a vent opening that connects to a venting valve member and provides a vent path which passively opens upon operation of the tissue sealant spray assembly, avoiding excessive pressure build-up within a body cavity. The concept of this patent application is similar in principle to that of Hoogenakker, where excess gas introduced into the abdominal cavity during the spray application of the biomaterial is removed through a passive actuation of a valve associated with the trocar vent valve. However, the same limitation exist for Redl as they do for Hoogenakker, where an available trocar gas valve port may not be available on a trocar if only one trocar with a gas valve port is used and the remaining trocars do not include a gas valve port. Additionally, in a single incision surgery where only one trocar is being used, only one gas valve port is available during the surgery and this gas valve port must be dedicated to the insufflator.

While biomaterial applicators have become increasingly important in minimally invasive surgeries, there is a continued need for an endoscopic biomaterial applicator that can provide a spray delivery of a given biomaterial while also safely minimizing the potential of over-pressurization within a patient's abdominal cavity during the introduction of a gas flow from the biomaterial applicator. Furthermore, there is a continued need for an endoscopic biomaterial applicator that is not dependent on the gas valve port of a surgical trocar to accomplish the management of gas pressure within the abdominal cavity. The present invention satisfies these needs.

SUMMARY OF THE INVENTION

The present invention will provide an endoscopic biomaterial applicator used during laparoscopic surgical procedures that utilizes pressurized gas to facilitate the spray application of a biomaterial while safely venting the additional volume of gas introduced into the abdominal cavity by endoscopic biomaterial applicator. This is accomplished utilizing a manifold, a plurality of channels, an elongated housing, a spray tip, a cannula gasket, and a gas release valve.

The present invention permits surgeons to introduce an endoscopic biomaterial applicator through a surgical trocar, creating an air tight seal, and then dispense one or a plurality of biomaterials into the surgical site. The surgeon will place the device into the trocar, where pressurized gas is channeled through the biomaterial applicator and through the spray tip for dispersing the biomaterial in a spray fashion.

The present invention will also utilize a gas release valve on the biomaterial applicator that is exposed to the internal pressure of the abdominal cavity, wherein the pressure within the abdominal cavity can be automatically released when spray actuation is initiated. Once spray actuation is initiated, the input gas will compress a control piston against a control spring, opening the gas release valve and venting the intra-abdominal pressure to the atmosphere. When spray actuation is terminated, the control spring will return the control piston to a closed position, preventing additional intra-abdominal pressure from venting to the atmosphere.

Alternatively, a check valve may be used to release gas from the body cavity. The various elements of the check valve determine its cracking pressure, such as the spring diameter, length, and material, providing a check valve that will open once the abdominal cavity pressure reaches a desired pressure threshold, typically between 5-20 mmHg. Gas is then released from the abdominal cavity, through the device, and out to the atmospheric outside of the patient. When the abdominal pressure is reduced below the cracking pressure of the check valve, the spring of the gas release valve will return the piston to a closed position, separating the pressure of the abdominal cavity and the atmospheric pressure.

The current invention will separate the gas flow introduced into the biomaterial applicator for dispersing the biomaterial in a spray fashion and the gas release valve such that the gas release valve will only be subjected to the internal pressure of the abdominal cavity and not the gas pressure of the inflow gas passing through the endoscopic applicator.

These and other objectives of the present invention will become obvious to those of ordinary skill in the art after reading the following detailed description of the preferred embodiments. It is to be understood that the foregoing general description and the following detailed description are exemplary, and are intended to provide further explanation of the invention as claimed.

DETAILED DESCRIPTION OF THE PREFERRED EMBODIMENT

Figure 1:
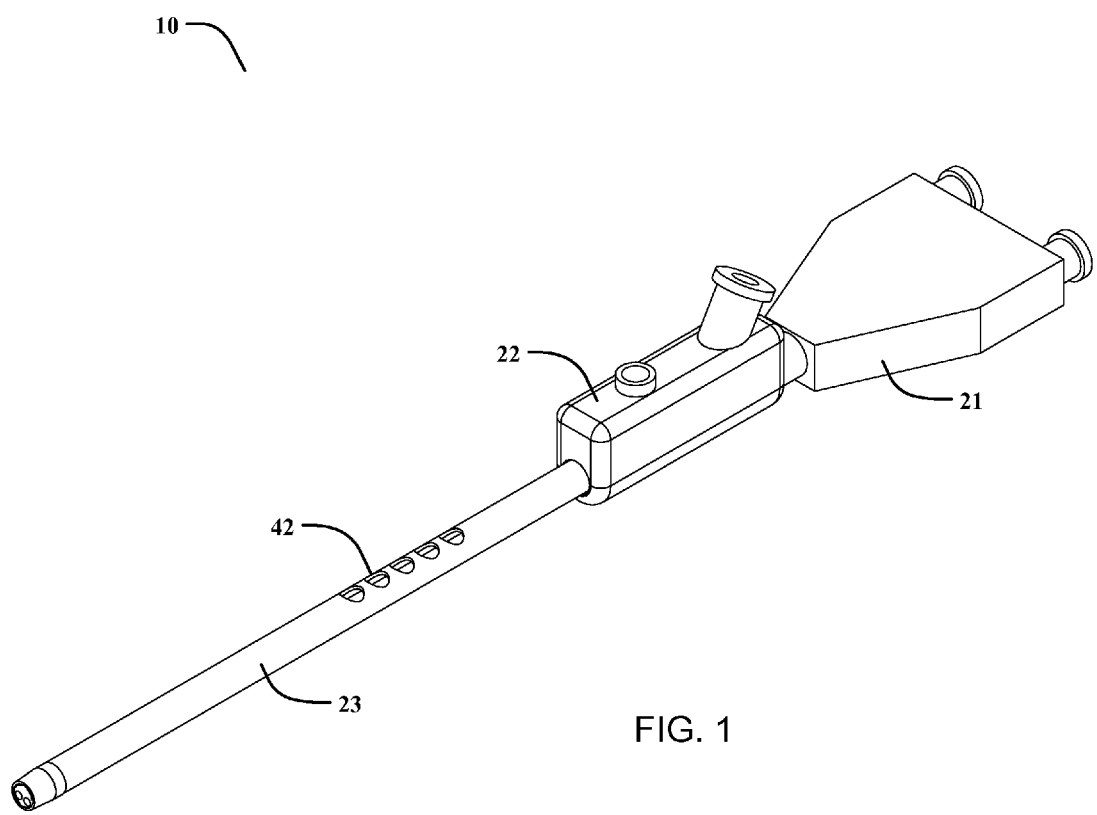
FIG. 1 is a front perspective view of the present invention.
Figure 2:
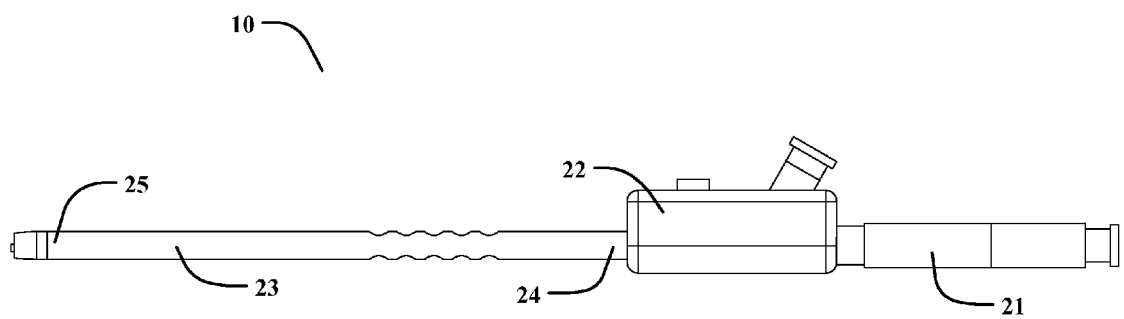
FIG. 2 is a side view of the present invention.
Figure 3:
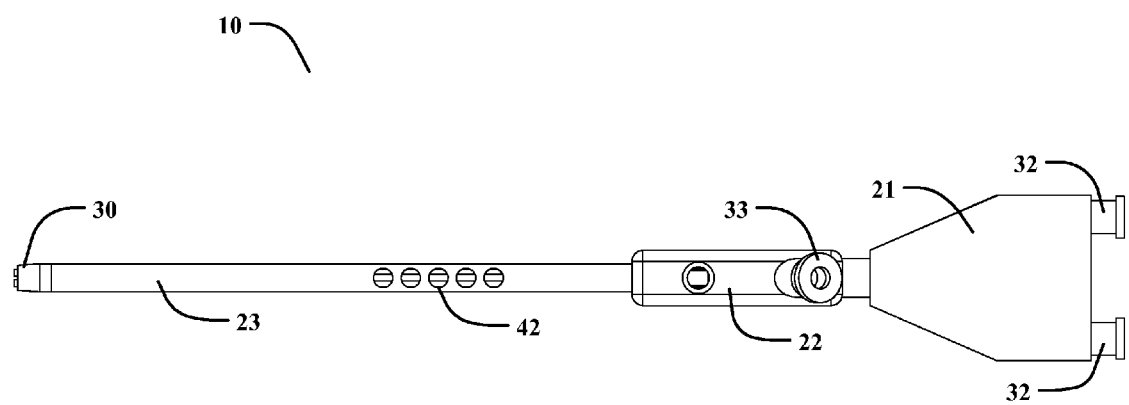
FIG. 3 is a top plan view of the present invention.
Figure 4:
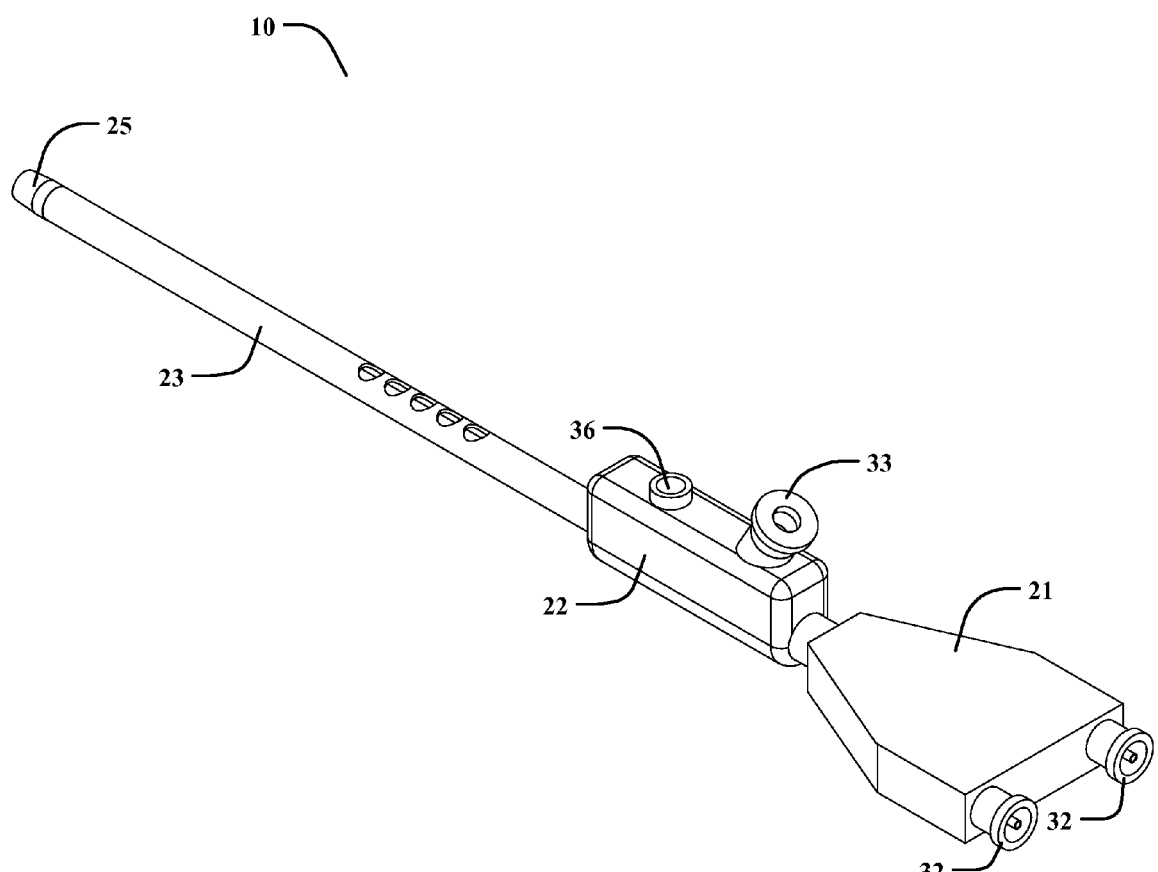
FIG. 4 is a rear perspective view of the present invention.
Figure 5:
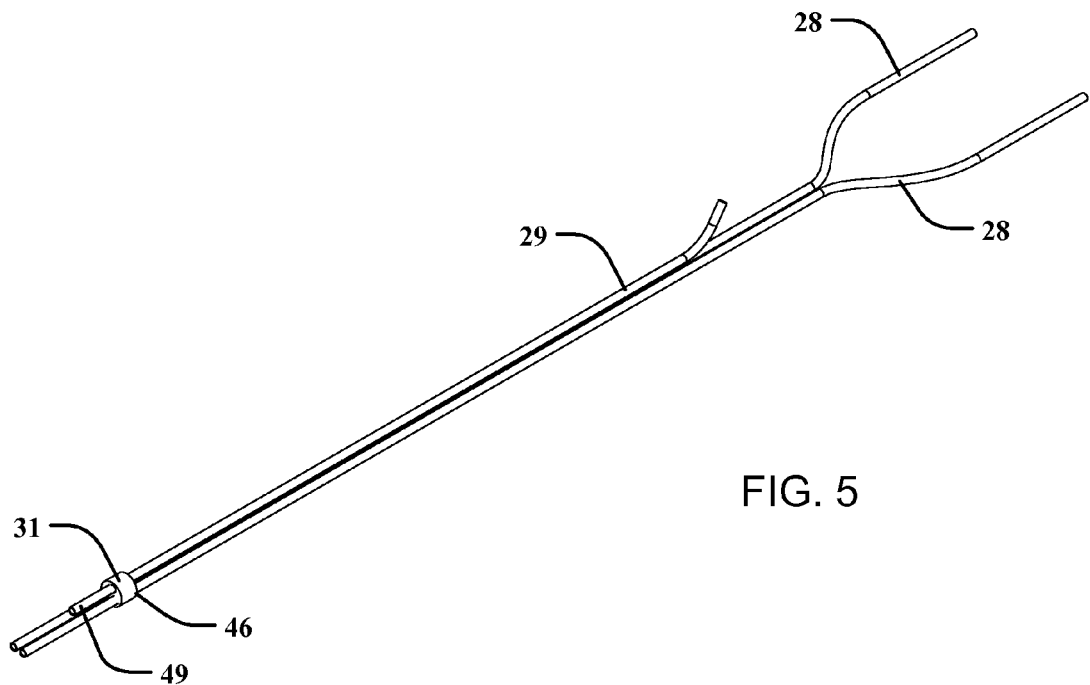
FIG. 5 is a perspective view of the present invention without manifold and housings.
Figure 6:
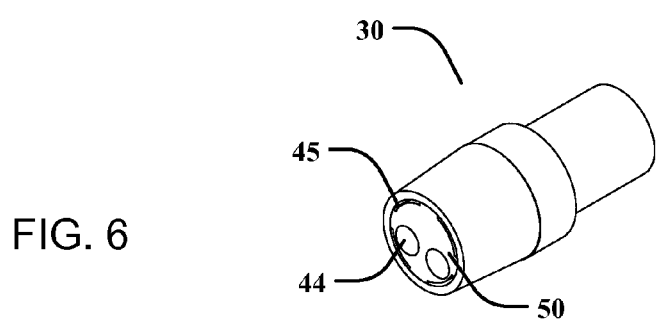
FIG. 6 is a close up perspective view of the spray tip.

Illustrative embodiments of the invention are described below. The following explanation provides specific details for a thorough understanding of and enabling description for these embodiments. One skilled in the art will understand that the invention may be practiced without such details. In other instances, well-known structures and functions have not been shown or described in detail to avoid unnecessarily obscuring the description of the embodiments.

Unless the context clearly requires otherwise, throughout the description and the claims, the words "comprise," "comprising," and the like are to be construed in an inclusive sense as opposed to an exclusive or exhaustive sense; that is to say, in the sense of "including, but not limited to." Words using the singular or plural number also include the plural or singular number respectively. Additionally, the words "herein," "above," "below" and words of similar import, when used in this application, shall refer to this application as a whole and not to any particular portions of this application. When the claims use the word "or" in reference to a list of two or more items, that word covers all of the following interpretations of the word: any of the items in the list, all of the items in the list and any combination of the items in the list.

The present invention 10 comprises a manifold 21, a vent housing 22, an elongated endoscopic housing 23 having proximal 24 and distal 25 ends, a gas release valve 26 positioned within said vent housing 22, one or more biomaterial channels 28 within said manifold 21 and elongated endoscopic housing 23, a gas channel 29 enclosed within said manifold 21, said vent housing 22, and elongated endoscopic housing 23, a spray tip 30, and a cannula gasket 31. These components work in conjunction to deliver biomaterial into a patient's 11 internal body cavity 12 during a laparoscopic procedure, where pressurized gas aids in dispersing the biomaterial in a spray fashion. In the preferred embodiment, the present invention 10 is adapted to simultaneously self-vent the additional volume of gas introduced by the biomaterial applicator 10. In an alternative embodiment, gas is self-vented when the intra-abdominal pressure reaches a threshold value, or setpoint cracking pressure, of the gas release valve 26. The manifold 21 and vent housing 22 can be generally described as a housing.

Biomaterial is delivered through a cannula 13 adapted for introduction through a surgical trocar 14, where the biomaterial channels 28 will carry the biomaterial component(s) from the manifold 21, through the elongated endoscopic housing 23, through the cannula gasket 31, and to the spray tip 30. A pressurized gas source 16 is connected to the manifold 21 or vent housing 22 through a gas attachment 33, where the pressurized gas is then delivered into the gas channel 29. The pressurized gas is then delivered through the elongated endoscopic housing 23 and released into the elongated endoscopic housing 23 at a proximal location 24 to the spray tip 30 and a distal location 46 to the cannula gasket 31. The pressurized gas will then exit through the spray tip 30, mixing and dispersing the biomaterial component(s) within the body cavity 12 of the patient 11. The cannula gasket 31 prevents the pressurized gas from flowing proximally 24 through the elongated endoscopic housing 23.

The manifold 21 comprises a top 47 and bottom 48 manifolds, which operate to enclose the biomaterial and gas channels 28, 29 within the manifold 21. The manifold 21 is adapted to receive a plurality of attachments 32, 33 for introducing biomaterial agents and pressurized gas into the biomaterial and gas channels, respectively. Alternatively, the gas channel 29 can be introduced through the vent housing 22. The vent housing 22 further comprises a vent cavity 34 adapted to enclose the gas release valve 26, an intake port 35 for introducing the intra-abdominal pressure to the gas release valve 26, and an exhaust port 36 for releasing said intra-abdominal pressure into the atmosphere. While the preferred embodiment utilizes two biomaterial attachments 32, one gas release valve 26, and one gas attachment 33, any number can be used. Once the biomaterial and gas delivery container(s) 15, 16 are attached to the manifold attachments 32, 33, the biomaterials and gases can be introduced into the manifold 21 and subsequently through the channels 28, 29.

The elongated endoscopic housing 23 is attached to the manifold 21 and vent housing 22 at its proximal end 24 and encloses the biomaterial and gas channels 28, 29 as they travel from the manifold 21 to the spray tip 30. Furthermore, the elongated endoscopic housing 23 is adapted to be inserted through a surgical trocar 14 for access to the internal cavity 12 of a patient 11. A plurality of internal abdominal apertures 42 are positioned on the elongated endoscopic housing 23 such that, when inserted into the surgical trocar 14, the abdominal apertures 42 are situated within the internal cavity 12 and not within the trocar delivery sheath 14 or exterior of the internal cavity 12. A single external vent aperture 43 is positioned at the proximal end 24 of the elongated endoscopic housing 23 and is fluidly connected with the intake port 35 of the vent cavity 34. When in use, the abdominal apertures 42 are exposed to the internal cavity 12 of the patient, and as such, to the pressure within the internal cavity 12. The pressurized gas will travel through the elongated endoscopic housing 23, equalizing the pressure within the elongated endoscopic housing 23 and the internal cavity 12 of the patient 11.

The gas release valve 26 is positioned on the manifold 21 or vent housing 22 and is aligned with the external vent aperture 43 such that, when in use, the gas release valve 26 is exposed to the pressure of the internal cavity 12. Therefore, the gas release valve 26 operates as a gateway between the pressure of the internal cavity 12 and atmospheric pressure. The gas release valve 26 is adapted to open and release a volume of gas from within the internal cavity 12 when gas is introduced into the system or when the pressure of the internal cavity 12 reaches the setpoint of the cracking pressure of the gas release valve 26, typically within a range of 5-20 mmHg.

Figure 7:
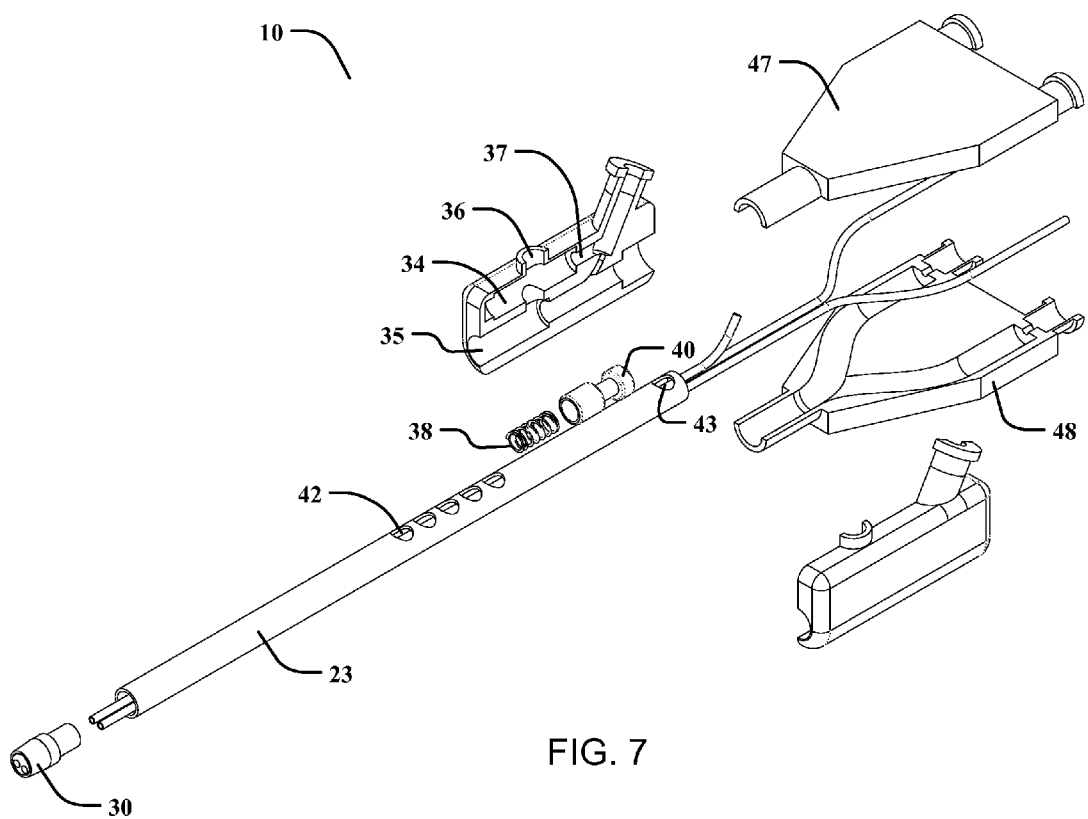
FIG. 7 is an exploded perspective view of the present invention with auto valve.
Figure 8:
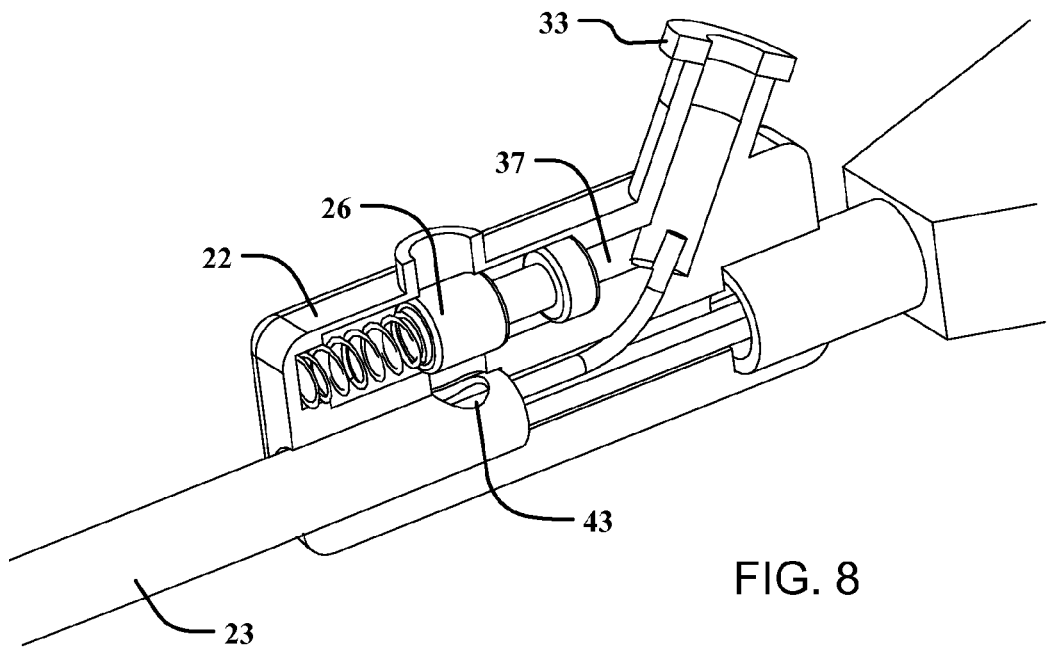
FIG. 8 is a sectional perspective view of the present invention with auto valve in a closed position.
Figure 9:
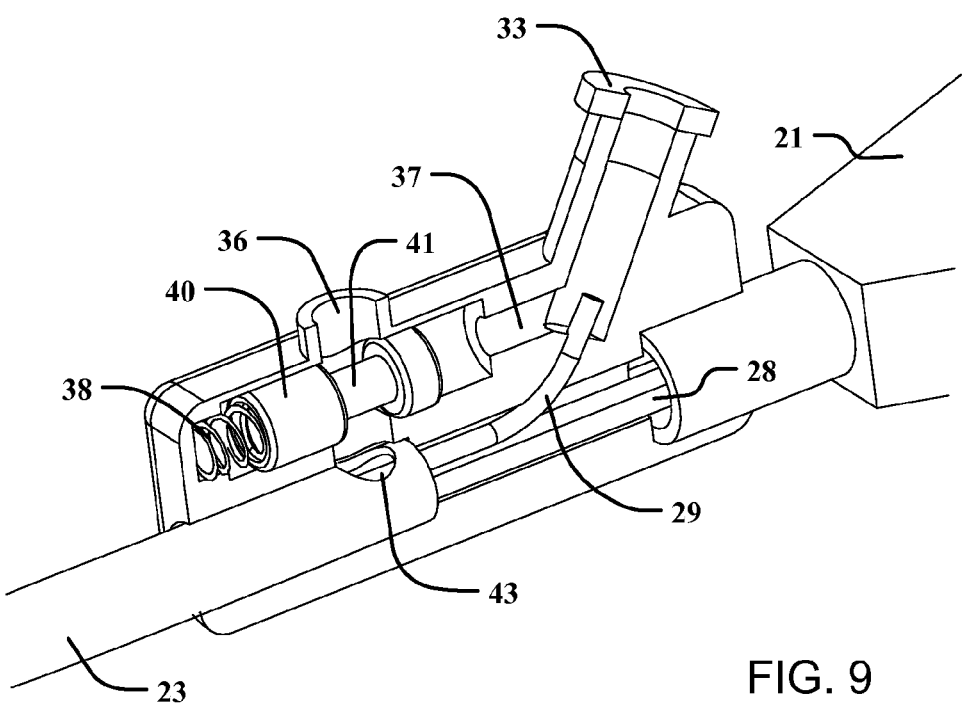
FIG. 9 is a sectional perspective view of the present invention with auto valve in an open position.

In the preferred embodiment, the gas release valve 26 comprises a 3-port auto valve (FIG. 7) having a control port 37 and control piston 40 with a control piston aperture 41. Here, a valve spring 38 will apply pressure onto the control piston 40 into the control port 37 and force the auto valve 26 into a closed position (FIG. 8). The control port 37 is fluidly connected to the gas channel 29 and gas attachment 33, whose gas pressure will inherently increase as the pressure from the gas channel 29 increases. Once this pressure exceeds the valve spring 38 pressure, or spring force pressure, the control piston 40 is forced against the valve spring 38 into an open position (FIG. 9), exposing the control piston aperture 41 and fluidly connecting the intake and exhaust ports 35, 36, permitting air flow venting therethrough.

Figure 10:
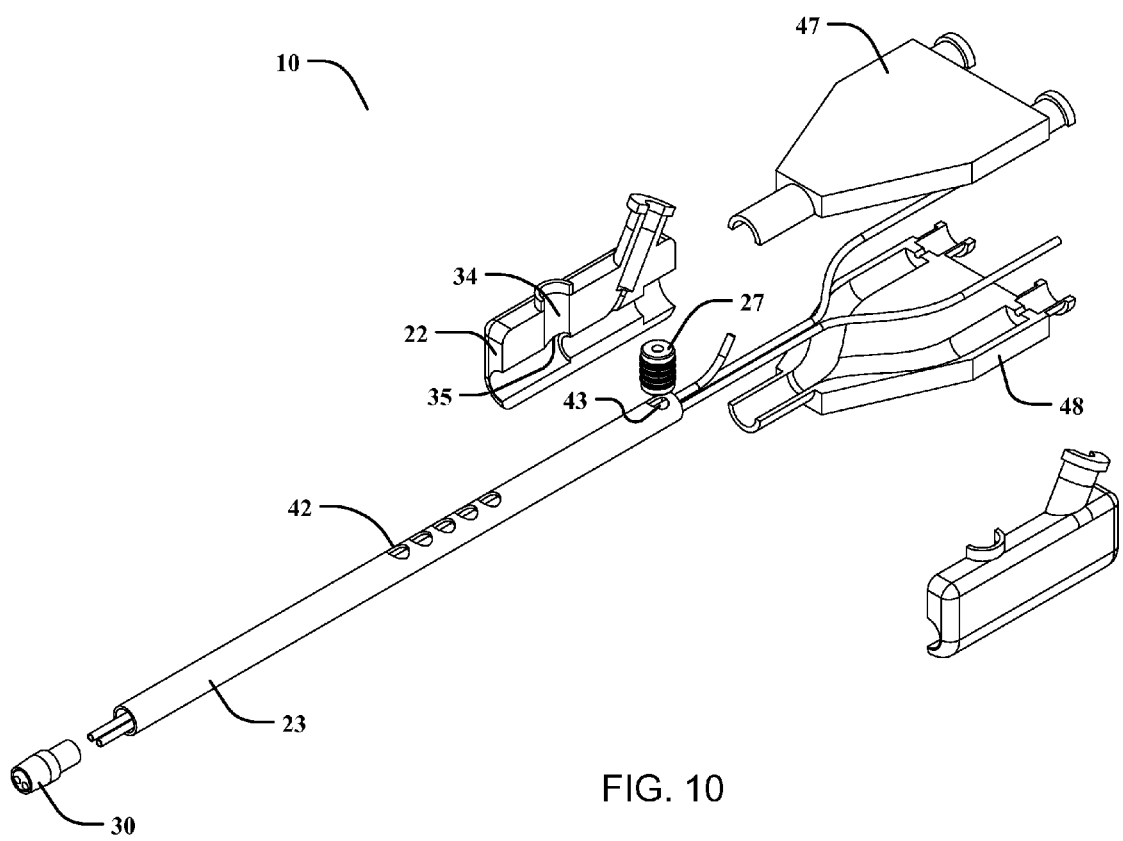
FIG. 10 is an exploded perspective view of the present invention with check valve.
Figure 11:
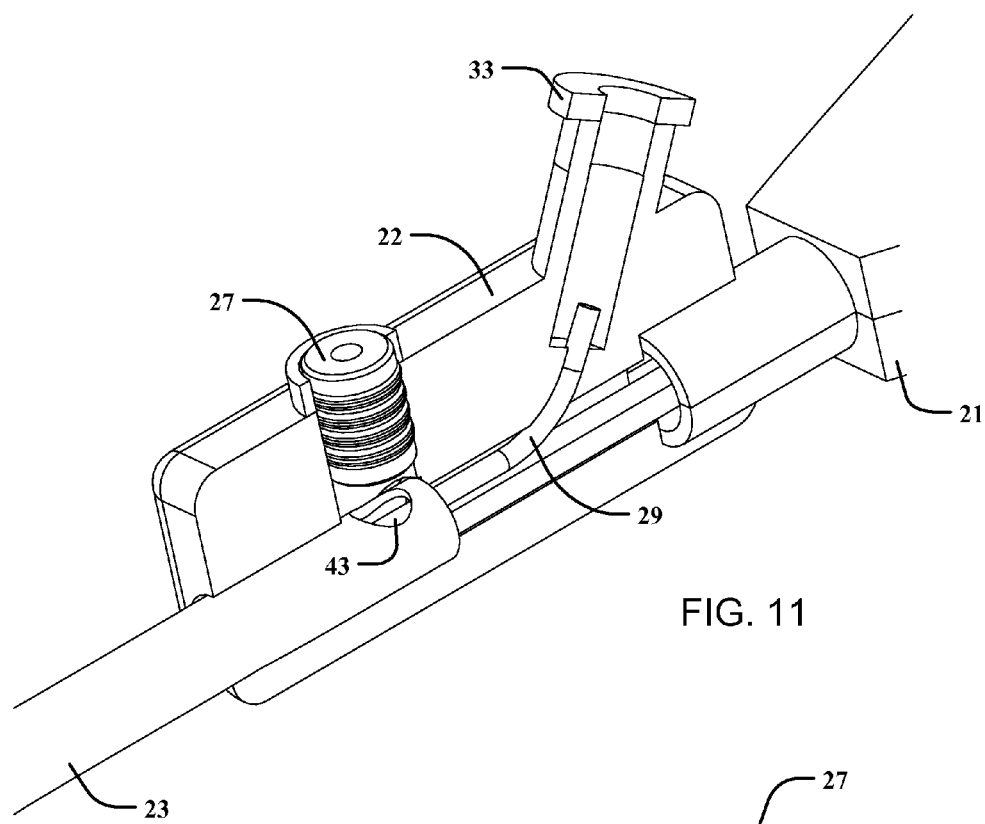
FIG. 11 is a sectional perspective view of the present invention with check valve.
Figure 12:
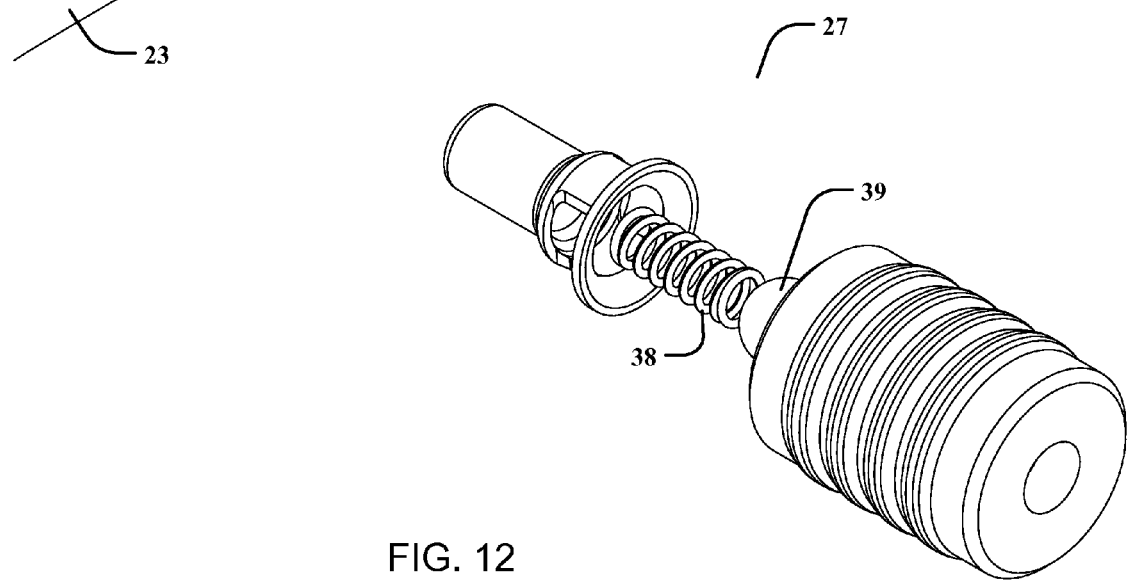
FIG. 12 is a close up exploded perspective view of the check valve.
Figure 13:
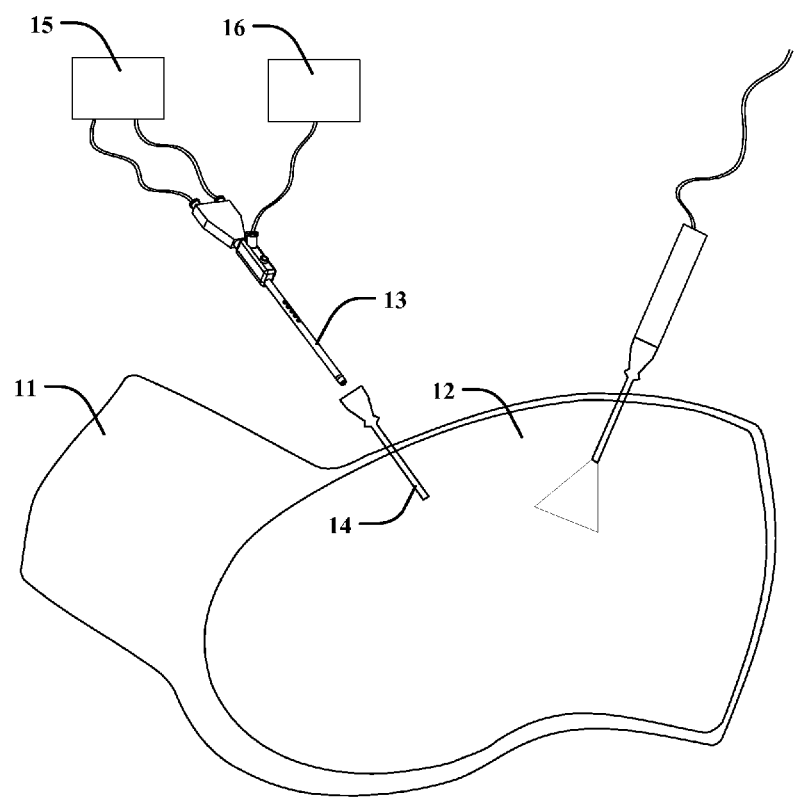
FIG. 13 is an illustration of the present invention is use during a laparoscopic procedure.

In an alternative embodiment, the gas release valve 26 comprises a 2-port check valve 27 (FIG. 10) having an adjustable setpoint cracking pressure, valve spring 38, and valve ball 39. Here, the valve spring 38 will apply pressure to the valve ball 39, with a pressure adjusting screw adapted to increase or decrease the pressure applied. Once the internal pressure exceeds the pressure of the valve spring 38, the check valve 27 is forced open and the gas is released into the atmosphere.

In yet a further alternative embodiment, the gas release valve 26 comprises a 2-port fixed pressure check valve 27 (FIG. 10) with a valve spring 38, and valve ball 39. Here, the valve spring 38 will apply pressure to the valve ball 39, where the valve spring 38 has been selected to provide a specific spring force tension that cannot be compressed to open the valve until a specific cracking pressure threshold is achieved. Once the internal pressure exceeds the pressure of the valve spring 38, the check valve 27 is forced open and the gas is released into the atmosphere.

In the check valve and fixed check valve 27 embodiments, the pressure of the internal cavity 12 and elongated endoscopic housing 23 are equivalent, permitting the check valves 27 to relieve the pressure from the internal cavity 12 until the pressure becomes equal or lower to the setpoint of the cracking pressure of the check valves 27. Once the pressure within the internal cavity 12 is reduced to equal or lower than the cracking pressure of the check valves 27, it will close and no longer allow the flow of gas to leave the internal cavity 12, thus sustaining the desired surgical distention.

The cannula gasket 31 is located inside the elongated endoscopic housing 23 near its distal end 25 and provides a gas tight seal between the gas ejected from the gas channel 29 and the gas release valve 26. The cannula gasket 31 is positioned distally to the abdominal apertures 42 in the elongated endoscopic housing 23 and proximally to the distal end 49 of the gas channel 29. This ensures that the gas pressure exiting the gas channel 29 is delivered to the spray tip 30 and then to the internal 12 cavity. The abdominal pressure can then only return through the abdominal apertures 42. The gas channel 29 and the biomaterial channels 28 travel through the cannula gasket 31 to the spray tip 30.

The spray tip 30 is mounted at the distal end 25 of the elongated endoscopic housing 23. The spray tip 30 also incorporates the biomaterial channels 28 which terminate coincident with the distal face 50 of the spray tip 30 through a plurality of spray apertures 44. The spray tip's 30 function is to expel the component(s) of the biomaterial while providing a circular or semi-circular flow of pressurized gas around the biomaterials from the gas channel 29 through a plurality of gas apertures 45. This circular "curtain" of air will then take the biomaterials with the gas flow and disperse the biomaterials in a spray fashion.

In a further alternative embodiment, a plurality of gas release valves 26 are positioned on the biomaterial applicator 10, wherein each gas release valve 26 will have a different cracking pressure. An adjustable rotating member (not pictured) attached to the proximal side 24 of the elongated endoscopic housing 23 will allow selection of a specific gas release valve 26 mounted in the manifold 21 or vent housing 22 in order to provide the surgeon with a selection of different cracking pressures. The adjustable rotating member (not shown) further comprises a plurality of vent apertures 43 fluidly connecting the gas release valves 26 with the pressure of the internal cavity 12. This rotating member (not shown) could be rotated such that the vent apertures 43 align with any given gas release valve 26 in the manifold 21 or vent housing 22.

While the above description contains specific details regarding certain elements, sizes, and other teachings, it is understood that embodiments of the invention or any combination of them may be practiced without these specific details. Specifically, although colors are designated in the above embodiments, any color may be used. These details should not be construed as limitations on the scope of any embodiment, but merely as exemplifications of the presently preferred embodiments. In other instances, well known structures, elements, and techniques have not been shown to clearly explain the details of the invention.

The above detailed description of the embodiments of the invention is not intended to be exhaustive or to limit the invention to the precise form disclosed above or to the particular field of usage mentioned in this disclosure. While specific embodiments of, and examples for, the invention are described above for illustrative purposes, various equivalent modifications are possible within the scope of the invention, as those skilled in the relevant art will recognize. Also, the teachings of the invention provided herein can be applied to other systems, not necessarily the system described above. The elements and acts of the various embodiments described above can be combined to provide further embodiments.

Changes can be made to the invention in light of the above "Detailed Description." While the above description details certain embodiments of the invention and describes the best mode contemplated, no matter how detailed the above appears in text, the invention can be practiced in many ways. Therefore, implementation details may vary considerably while still being encompassed by the invention disclosed herein. As noted above, particular terminology used when describing certain features or aspects of the invention should not be taken to imply that the terminology is being redefined herein to be restricted to any specific characteristics, features, or aspects of the invention with which that terminology is associated.

While certain aspects of the invention are presented below in certain claim forms, the inventor contemplates the various aspects of the invention in any number of claim forms. Accordingly, the inventor reserves the right to add additional claims after filing the application to pursue such additional claim forms for other aspects of the invention.

What is claimed is:

1. A self-venting endoscopic biomaterial applicator comprising:

- a manifold;
- a vent housing;
- an elongated endoscopic housing having proximal and distal ends, said proximal end attached to said manifold;
- a gas release valve positioned within said vent housing;
- a plurality of biomaterial channels enclosed within said manifold and elongated endoscopic housing; and
- a gas channel enclosed within said manifold and elongated endoscopic housing;
- wherein said applicator is inserted into a body cavity of a patient through a trocar for introducing biomaterial and pressurized gas into said patient, and wherein said introduction of biomaterial and pressurized gas actuates said gas release valve, simultaneously releasing pressurized gas from the body cavity as biomaterial and pressurized gas is introduced.

2. The self-venting endoscopic biomaterial applicator of claim 1, wherein said manifold further comprises a plurality of attachments for introducing biomaterial agents into said biomaterial channel.

3. The self-venting endoscopic biomaterial applicator of claim 2, wherein said vent housing further comprises:

- an attachment for introducing pressurized gas into said gas channel; and
- a vent cavity adapted to enclose said gas release valve, said vent cavity further comprising intake and exhaust ports.

4. The self-venting endoscopic biomaterial applicator of claim 3, wherein said elongated endoscopic housing further comprises:

- a plurality of abdominal apertures adapted to expose said elongated endoscopic housing to said intra-abdominal pressure; and
- a vent aperture adapted to expose said gas release valve to said intra-abdominal pressure, said intake port fluidly connected with said vent aperture.

5. The self-venting endoscopic biomaterial applicator of claim 4, wherein said gas release valve further comprises an auto valve comprising a control piston and control port adapted to restrict flow from said intake port to said exhaust port, said control port fluidly connected with said gas channel and gas attachment for automatically venting intra-abdominal pressure when gas actuation is initiated and terminating venting when gas actuation is terminated.

6. The self-venting endoscopic biomaterial applicator of claim 4, wherein said gas release valve further comprises a check valve comprising a valve ball and valve spring adapted to restrict flow from said intake port to said exhaust port and adapted to release said pressurized gas when said intra-abdominal pressure reaches said adjustable pressure threshold.

7. The self-venting endoscopic biomaterial applicator of claim 6, wherein said check valve further comprises an adjustable pressure threshold having a range of 5-20 mmHg.

8. The self-venting endoscopic biomaterial applicator of claim 1, further comprising:
 a spray tip attached to said distal end of said elongated endoscopic housing;
 a plurality of spray apertures adapted to receive said biomaterial channels; and
 a plurality of gas apertures adapted to release said pressurized gas from said gas channel.

9. The self-venting endoscopic biomaterial applicator of claim 8, further comprising a cannula gasket positioned between said abdominal apertures and said spray tip adapted to separate said spray tip and said elongated endoscopic housing, preventing said pressurized gas from flowing proximally through said elongated endoscopic housing.

10. A self-venting endoscopic biomaterial applicator comprising:
 a housing exposed to intra-abdominal pressure;
 a gas release valve positioned within said housing;
 a plurality of biomaterial and gas channels enclosed within said housing;
 a plurality of abdominal apertures adapted to expose said housing to said intra-abdominal pressure; and
 a vent aperture adapted to expose said gas release valve to said intra-abdominal pressure;
 wherein said applicator is inserted into a body cavity of a patient through a trocar for introducing biomaterial and pressurized gas into said patient, and wherein said pressurized gas is released through said gas release valve simultaneously with the introduction of said pressurized gas into said body cavity.

11. The self-venting endoscopic biomaterial applicator of claim 10, wherein said gas release valve further comprises an auto valve fluidly connected with said gas channel for automatically venting intra-abdominal pressure when gas actuation is initiated and terminating venting when gas actuation is terminated.

12. The self-venting endoscopic biomaterial applicator of claim 10, wherein said gas release valve further comprises a check valve comprising a valve ball and valve spring adapted to restrict flow from said intake port to said exhaust port and adapted to release said pressurized gas when said intra-abdominal pressure reaches said adjustable pressure threshold.

* * * * *